(12) United States Patent
Pugh et al.

(10) Patent No.: US 9,244,013 B2
(45) Date of Patent: Jan. 26, 2016

(54) METHOD OF QUANTIFYING UV DISINFECTING DOSES APPLIED TO AN OPHTHALMIC LENS USING INDICATORS

(71) Applicant: Johnson & Johnson Vision Care, Inc., Jacksonville, FL (US)

(72) Inventors: Randall B. Pugh, Jacksonville, FL (US); Edward R. Kernick, Jacksonville, FL (US); Karson S Putt, Jacksonville, FL (US); Terry O'Brien, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 222 days.

(21) Appl. No.: 13/924,693

(22) Filed: Jun. 24, 2013

(65) Prior Publication Data

US 2014/0004609 A1    Jan. 2, 2014

Related U.S. Application Data

(60) Provisional application No. 61/665,960, filed on Jun. 29, 2012.

(51) Int. Cl.
| | |
|---|---|
| *G01N 21/64* | (2006.01) |
| *A61L 2/28* | (2006.01) |
| *A61L 12/06* | (2006.01) |
| *G01N 31/22* | (2006.01) |
| *G01J 1/50* | (2006.01) |

(52) U.S. Cl.
CPC ............. *G01N 21/6428* (2013.01); *A61L 2/28* (2013.01); *A61L 12/063* (2013.01); *G01J 1/50* (2013.01); *G01N 31/226* (2013.01)

(58) Field of Classification Search
CPC ..... G01J 1/50; G01N 21/6428; G01N 31/226; A61L 2/28; A61L 12/063
USPC ............................................................. 436/1
See application file for complete search history.

(56) References Cited

U.S. PATENT DOCUMENTS

| | | | | |
|---|---|---|---|---|
| 2,738,429 | A | | 3/1956 | Goldblith |
| 3,787,687 | A | * | 1/1974 | Trumble ............... 250/474.1 |
| 3,852,032 | A | * | 12/1974 | Urbach ............ A61L 12/063 |
| | | | | 351/159.6 |
| 4,063,890 | A | * | 12/1977 | Baron ............. A61L 12/063 |
| | | | | 250/455.11 |
| 4,308,459 | A | * | 12/1981 | Williams .............. 250/474.1 |
| 4,829,187 | A | * | 5/1989 | Tomita et al. ......... 250/474.1 |
| 4,918,317 | A | * | 4/1990 | Hess ................... B01J 13/04 |
| | | | | 250/474.1 |
| 5,028,792 | A | * | 7/1991 | Mullis ................... 250/474.1 |
| 5,120,499 | A | * | 6/1992 | Baron ............. A61L 12/026 |
| | | | | 250/455.11 |

(Continued)

FOREIGN PATENT DOCUMENTS

| | | | |
|---|---|---|---|
| JP | 2003-93481 | * | 4/2003 |
| JP | 2003-311762 | * | 4/2005 |

OTHER PUBLICATIONS

Dorcas, M. J. et al, Jornal of the American Chemical Society 1927, 49, 3081-3086.*

(Continued)

*Primary Examiner* — Arlen Soderquist

(57) ABSTRACT

The presented invention describes the development of a measuring method based on the degradation of various chromophores/fluorophores that can be used as quantitative method to elucidate the UV dose within a liquid or as a qualitative visual color-changing chemical indicator of UV sterilization is described.

1 Claim, 12 Drawing Sheets

(56) References Cited

U.S. PATENT DOCUMENTS

| | | | | |
|---|---|---|---|---|
| 5,144,144 | A * | 9/1992 | Borovsky | A61L 12/063 250/455.11 |
| 5,387,798 | A * | 2/1995 | Funakoshi et al. | 250/474.1 |
| 5,581,090 | A * | 12/1996 | Goudjil | 250/474.1 |
| 6,255,659 | B1 * | 7/2001 | Sandison | 250/474.1 |
| 6,287,518 | B1 * | 9/2001 | Ignacio et al. | 422/86 |
| 6,465,799 | B1 * | 10/2002 | Kimble | A61L 2/10 250/455.11 |
| 6,475,433 | B2 * | 11/2002 | McGeorge et al. | 422/24 |
| 6,586,172 | B1 * | 7/2003 | Gunn | A61L 2/0011 356/426 |
| 6,596,542 | B1 * | 7/2003 | Schulz | 436/1 |
| 6,746,739 | B2 * | 6/2004 | Andrews et al. | 428/35.7 |
| 7,956,334 | B2 * | 6/2011 | Morita | C02F 1/32 250/474.1 |
| 2001/0048891 | A1 | 12/2001 | McGeorge et al. | |
| 2002/0028861 | A1 * | 3/2002 | Andrews et al. | 524/100 |
| 2003/0075490 | A1 * | 4/2003 | Lifschitz | C02F 1/325 210/192 |
| 2003/0148526 | A1 * | 8/2003 | Schulz | 436/10 |
| 2003/0155531 | A1 * | 8/2003 | Clark | A23K 3/26 250/492.1 |
| 2004/0214335 | A1 * | 10/2004 | Li | A61L 2/0011 436/57 |
| 2005/0013729 | A1 * | 1/2005 | Brown-Skrobot | A61L 2/10 422/24 |
| 2005/0028848 | A1 * | 2/2005 | Lai | A61L 12/026 134/184 |
| 2005/0079096 | A1 * | 4/2005 | Brown-Skrobot | A61L 2/10 422/24 |
| 2005/0254992 | A1 * | 11/2005 | Jenkins | A61L 2/24 422/24 |
| 2006/0045796 | A1 * | 3/2006 | Anderle | A23L 3/26 422/3 |
| 2006/0257877 | A1 * | 11/2006 | Anderle | A61L 2/0011 435/6.18 |
| 2006/0289796 | A1 | 12/2006 | Havens | |
| 2008/0259315 | A1 * | 10/2008 | Mersch | 356/51 |
| 2009/0045352 | A1 * | 2/2009 | Morita | C02F 1/32 250/474.1 |
| 2009/0047176 | A1 * | 2/2009 | Cregger et al. | 422/28 |
| 2009/0280028 | A1 * | 11/2009 | Muggli | A61L 2/10 422/24 |
| 2010/0074800 | A1 * | 3/2010 | Miwa et al. | 422/56 |
| 2010/0326484 | A1 * | 12/2010 | Wu | A61L 2/025 134/56 R |
| 2010/0329950 | A1 * | 12/2010 | Faran | 422/400 |
| 2011/0024649 | A1 * | 2/2011 | Merkle | 250/492.1 |
| 2011/0284773 | A1 | 11/2011 | Pugh et al. | |
| 2012/0142527 | A1 * | 6/2012 | Smyth et al. | 503/201 |

OTHER PUBLICATIONS

Ozaki, A. et al, Food and Chemical Technology 1998, 36, 811-817.*
Gayan, E. et al, Innovative Food Science and Emerging Technologies 2011, 12, 531-541.*
Brauer, H.-D. et al, Photochemistry and Photobiology 1983, 37, 587-591.*
European Search Report for corresponding Application No. EP13174362.7 dated Oct. 24, 2013.
Putt, K.S., et al., "The Use of Chromophore and Fluorophore Degradation to Quantitate UV Dose: FD&C Dyes as Chemical Identicators for UV Sterilization", XP-002715324, Journal of Microbiological Methods 91 (2012), pp. 215-221.

* cited by examiner

| Dye | Dose Quantitation Range (mW*s/cm²) |
|---|---|
| Erythrosin B | 0 - 400 |
| Indigo Carmine | 0 - 1200 |
| Fluorescein | 0 - 1800 |
| Fast Green | 0 - 3500 |
| Allura Red | 0 - 4000 |
| Tartrazine | 0 - 12,000 |

FIG. 5(A)

| Dose mW*s/cm² | Bacteria | Fungus | Protozoa | Virus |
|---|---|---|---|---|
| 0 | Vibrio cholerae (20)<br>Escherichia Coli (43)<br>Mycobacterium tuberculosis (47)<br>Staphylococcus aureus (50)<br>Pseudomonas aeruginosa (82)<br>Serratia marcescens (126)<br>Francisella tularensis (332)<br>Salmonella typhimurium (354)<br>Bacillus anthracis - spore (493)<br>Streptococcus pneumoniae (562) | Blastomyces dermatitidis (168)<br>Candida albicans (250)<br>Fusarium solani - spore (376)<br>Aspergillus flavus - spore (600)<br>Aspergillus amstelodami - spore (650) | Cryptosporidium pavrum (20)<br>Giardia lamblia (29) | Herpes Simplex 2 (53)<br>Herpes Simplex 1 (60)<br>Hepatitis A (126)<br>Poliovirus type 1 (133)<br>Epstein-Barr (194)<br>Bacteriophage MS2 (288)<br>HIV (336)<br>Adenovirus (560) |
| 500 | | Cladosporium trichoides (1344)<br>Scopulariopsis brevicaulis (1506)<br>Scopulariopsis brevicaulis (1506)<br>Aspergillus niger - spore (1608)<br>Aspergillus fumigatus (1665) | | Polyomavirus (695)<br>Human Cytomegalovirus (790) |
| 1000 | Bacillus atrophaeus - spore (1588) | | Acanthamoeba castellani (1198) | SV40 (1104) |
| 2500 | Bacillus thuringiensis (2763) | Rhizopus nigricans - spore (3600) | | |
| 5000 | | Stachybotrys chartarum (6690) | | SARS-CoV (3655) |

| Erythrosin B 10 µg/mL | Indigo Carmine 100 µg/mL | Erythrosin B 100 µg/mL |
|---|---|---|

METHOD OF QUANTIFYING UV DISINFECTING DOSES APPLIED TO AN OPHTHALMIC LENS USING INDICATORS

CROSS-REFERENCE TO RELATED APPLICATION

This application claims the benefit of U.S. Provisional Application No. 61/665,960 filed Jun. 29, 2012.

FIELD OF THE INVENTION

The present invention relates to the field of sterilization and, more specifically, disinfecting an Ophthalmic Lens using one or more programmed UV disinfecting doses.

BACKGROUND OF THE INVENTION

Currently, the disinfection of an ophthalmic lens includes a variety of liquid chemicals that in some cases can react with particle buildup and microbial organisms to achieve sterilization. However, in many cases the use of these chemical solutions may not achieve the sterilization and additionally remain in the ophthalmic lens to interact with the user's eye. The interaction may have some adverse effects, such as for example, cause discomfort or burning, affect the tear film chemistry balance, etc.

Consequently, it is desired that new improved sterilization methods and apparatus are developed that can overcome side effects and limitations, to fulfill long felt sterilization needs in the field of ophthalmic lenses.

SUMMARY OF THE INVENTION

The present invention relates to a method to obtain a quantitative measurement of ultraviolet (UV) irradiation doses. More specifically, where the dose can be measured within container or vessel used in the implementation of UV sterilization.

In some aspects of the present invention, the development of a measuring method based on the degradation of various chromophores/fluorophores that can be used as a quantitative method to elucidate the UV dose within a liquid or as a qualitative visual color-changing chemical indicator of UV sterilization is described.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention.

FIG. 5(A) are exemplary visual changes of Eyrthosin B and Indigo Carmine after exposure to 254 nm UV light and the 12 log overkill sterilization dose (number in parenthesis) for various UV biological indicators and human pathogens.

FIG. 6(A) shows the Fluorescein fluorescence standard curve (ex/em 490 nm/520 nm).

FIG. 6(B) shows the Allura Red UV/Vis absorbance spectra.

FIG. 6(C) shows the Allura Red absorbance standard curve.

FIG. 6(D) shows the Indigo Carmine UV/Vis absorbance spectra.

FIG. 6(E) shows the Indigo Carmine absorbance standard curve.

FIG. 6(F) shows the Erythrosin B UV/Vis absorbance spectra.

FIG. 6(G) shows the Erythrosin B absorbance standard curve.

FIG. 6(H) shows the Tartrazine UV/Vis absorbance spectra.

FIG. 6(I) shows the Tartrazine absorbance standard curve.

FIG. 6(J) shows the Fast Green UV/Vis absorbance spectra.

FIG. 6(K) shows the Fast Green absorbance standard curve.

DETAILED DESCRIPTION OF THE PREFERRED EMBODIMENTS

Figure 1A:
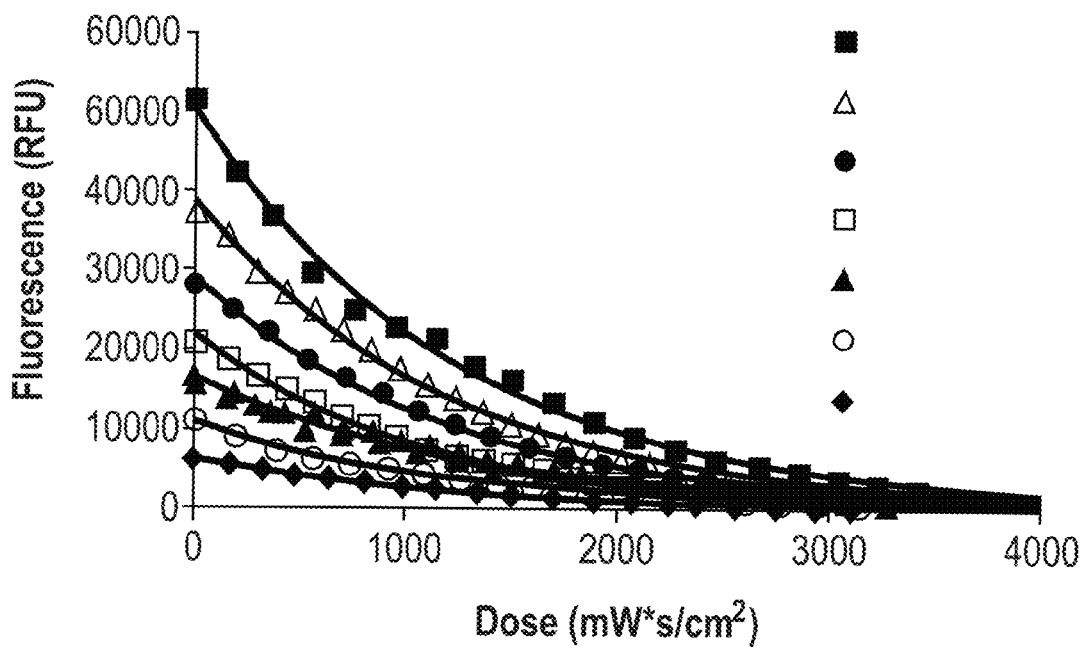
FIG. 1 exemplary curves of independent experiments performed depicting A.) The loss of fluorescence (ex./em. 490/520 nm) of various concentrations of fluorescein upon irradiation with known doses of 254 nm UV light. B.) All fluorescein degradation curves collapse to the same curve when raw fluorescence is converted to a percentage of the starting fluorescence value.

The present invention provides for a method of quantifying different doses of UV disinfection. In the following sections, detailed descriptions of embodiments of the invention are given. The description of both preferred and alternative embodiments though detailed are exemplary embodiments only, and it is understood to those skilled in the art that variations, modifications, and alterations may be apparent. It is therefore to be understood that said exemplary embodiments do not limit the broadness of the aspects of the underlying invention. Method steps described herein are listed in a logical sequence in this discussion; however, this sequence in no way limits the order in which they may be implemented unless specifically stated.

Definitions

"Ophthalmic Lens" as used herein and sometimes referred to as "Lens", means any ophthalmic device that resides in or on the eye. These devices may provide optical correction or may be cosmetic. For example, the term Lens may refer to a contact Lens, intraocular Lens, overlay Lens, ocular insert, optical insert or other similar device through which vision is corrected or modified, or through which eye physiology is cosmetically enhanced (e.g., iris color) without impeding vision. In some embodiments, the preferred Lenses of the invention are soft contact Lenses and are made from silicone elastomers or hydrogels, which include but are not limited to silicone hydrogels, and fluorohydrogels.

The accurate measurement of ultraviolet (UV) irradiation, especially within a container or vessel is one of the challenges facing the broad implementation of UV sterilization. Biological indicators can provide a method to determine whether an applied UV dose has the necessary efficacy to achieve sterilization. To overcome some of the challenges of using a biological indicator, chemical indicators based upon the degradation of food, drug and cosmetic (FD&C) were developed. In this work, the relationship between UV dose and dye degradation was elucidated and used to create standard curves. With this relationship known, the degradation of various dyes can be used as a quantitative measurement system. The use of dye degradation as a measurement of UV dose is especially useful when the levels of UV irradiation within a container cannot be measured directly. Additionally, due to the highly colored nature of the FD&C dyes, the visual changes present upon dye irradiation can be used as a qualitative visual indicator of the UV dose.

Germicidal ultraviolet (UV) bulbs have been recognized by the medical industry as a means for the disinfection and sterilization of medical instruments for well over 60 years. Since that time, UV light has been used as a disinfectant and sterilization agent for a number of different solid, liquid and gaseous materials. In particular, this technology has found extensive use in the treatment of drinking water during the past two decades.

Although germicidal bulbs have enjoyed widespread usage, one of the main challenges of using UV light to disinfect or sterilize liquids is the accurate determination of the UV dose within the liquid. Measuring a repeatable and reproducible UV dose was an issue when germicidal bulbs were first proposed as a sterilization method. While the energy per unit area imparted to a container of liquid is easily calculated from the power of the UV source and the exposure time, calculating the energy within the solution is not so trivial. Unfortunately, even today UV dose measurement standardization remains elusive with many new measurement methodologies being published.

The average dose (Davg) of UV light within a liquid can be calculated from the length of exposure (t) multiplied by the average intensity (Iavg): Davg=Iavg*t. The average intensity is calculated using the following equation: Iavg=Io*(1−e−A*L)/(A*L), where A is the absorbance of the liquid per centimeter and L is the path length of the solution being irradiated. However, this calculation is only valid for a homogeneous solution. The UV absorbance of materials within the solution itself or in the packaging containing the solution can create a very uneven dose when irradiated. The UV shadows created can provide locations where microorganisms are not effectively killed. Recently, computer modeling/simulations have been created in an attempt to better predict the dose and efficacy of UV in solutions with less than desired results. Due to the difficulties of obtaining an accurate dose and predicting the anti-microbial efficacy of a dose within a liquid, there is a clear need for additional quantitative measurement methods.

In addition to quantitative measurements, qualitative visual indicators are commonly used in sterilization processes. While biological indicators of UV disinfection and sterilization have been developed and are generally regarded as the most definitive test for sterilization, they suffer some disadvantages over chemical indicators, namely the delay in obtaining results, cost and potential for contamination. These disadvantages can limit the usefulness of biological indicators in some circumstances. While other forms of sterilization, such as steam and chemical have effective chemical indicators, the commercial availability of UV chemical indicators is lacking. There have been reports of fluorescently labeled microspheres and silica used to determine the dose within UV reactors and the degradation of free chlorine has been proposed as a method to quantitate the UV dose in solution. However, these chemical degradation techniques all have the ability to quantitate UV dose in solution, but lack the qualitative changes that can be observed with the naked-eye common to other chemical indicators.

Herein we describe the development of a measuring system based on the degradation of various chromophores/fluorophores that can be used as a quantitative method to elucidate the UV dose within a liquid or as a qualitative visual color-changing chemical indicator of UV sterilization.

Allura Red AC and Sunset Yellow FCF were purchased from the Tokyo Chemical Industry (Tokyo, Japan). Erioglaucine was purchased from Spectrum (Gardena, Calif.). Erythrosin B, Tartrazine and Fast Green FCF were purchased from Alfa Aesar (Ward Hill, Mass.). Indigo Carmine was purchased from Amresco (Solon, Ohio). Fluorescein sodium salt was purchased from Sigma (St. Louis, Mo.). NIST certified UV germicidal detector PMA2122 and data logger PMA2100 were purchased from Solar (Glenside, Pa.). UV bulbs were purchased from LCD Lighting (Orange, Conn.). TableCurve2D was purchased from Systat Software (San Jose, Calif.). Tryptic soy broth, tryptic soy agar, SAB-DEX broth and SA-DEX agar were purchased from Northeast Laboratories (Waterville, Me.). Corning clear 96-well plates #3585, quartz semi-micro cuvettes, petri dishes and all other materials were purchased from VWR (Atlanta, Ga.).

1 mL of a 10 µg/mL dye solution in DI water was added to a quartz cuvette. The UV/Vis absorbance spectra were read in a Molecular Devices M5 (Sunnyvale, Calif.) from 200 to 800 nm every 2 nm. The maximum peak absorbance in the visible region was determined for each dye.

100 µL of various concentrations of dye solution in DI water were added in triplicate to the wells of a 96-well plate. The 96-well plate absorbance was read at the appropriate wavelength on a Molecular Devices M5.

1 mL of various concentrations of fluorescein in DI water was added to quartz fluorescence cuvettes. The fluorescence intensity of each cuvette was measured with a Molecular Devices M5 with an excitation of 490 nm, an emission of 520 nm and a cutoff filter of 515 nm. The cuvettes were irradiated for various amounts of time with a germicidal UV bulb in a custom fixture. The bulb power, measured in µW/cm² was recorded before and after each irradiation cycle. The fluorescence intensity was measured again exactly as described above. The dose was calculated by multiplying the bulb power with the time. Decay curves were fitted with TableCurve2D using the 8119 DecayN equation with the form of $y=(b^{1-d}+cdx-cx)^{1/(1-d)}+a$.

1 mL of various concentrations of each dye in DI water was added to quartz cuvettes. The absorbance of each cuvette was measured with a Molecular Devices M5 at the maximum peak wavelength for each dye. The cuvettes were irradiated for various amounts of time with a germicidal UV bulb in a custom fixture. The bulb power, measured in µW/cm² was recorded before and after each irradiation cycle. The absorbance was measured again exactly as described above. The dose was calculated by multiplying the bulb power with the time. Curves were fitted exactly as described above.

A lawn of organisms was grown on a petri dish containing tryptic soy agar for the bacteria or SAB-DEX agar for *C. albicans* overnight at 35° C. The cells were scraped from the petri dish and transferred into 5 mL of Dulbecco's phosphate buffered saline (DPBS) containing 0.05% Tween 80 (v/v) (TDPBS). The absorbance of the organisms was read and compared to a standard curve. The cells were then diluted to the appropriate concentration as required for each specific experiment.

The inoculum for each organism was adjusted to ~$10^6$ CFU/mL in TDPBS. 1.5 mL of inoculum was added to a semi-micro quartz cuvette. The cuvettes were unevenly wrapped with various types and thicknesses of plastic wrap to create a container with varying amounts of UV absorbance. The UV bulb power was measured and the time adjusted such that each cuvette container was irradiated for a total dose of 250 mW*s/cm². The number of viable organisms was enumerated as described below. To the exact same cuvette container, a 10 µg/mL Erythrosin B solution was added and irradiated exactly as described above. After irradiation, the absorbance of the dye was measured at 525 nm and the corresponding dose was calculated using the fitted curve generated above.

100 µL of organism was added to each of six wells of Row A in a 96-well plate. 90 µL of SAB-DEX or TSB was added to rows B-H of the plate. A 1:10 serial dilution was created by transferring 10 µL from row A into the row B followed by a mixing. This pattern was repeated down the plate. 100 µL of SAB-DEX or TSB then was added to all wells. The plates were incubated for 48 hours at 35° C. The absorbance of each well was read using a Molecular Devices SpectraMax 384Plus. The wells were deemed either positive or negative for growth and the original concentration of organisms was calculated using the most probable number method.

1 mL of a 10 or 100 µg/mL solution of Erythrosin B or a 100 µg/mL solution of Indigo Carmine dye in DI water was added to a quartz cuvette. The UV bulb power was measured and the time adjusted such that each cuvette was irradiated for the specified dose. Cuvettes were photographed before and after irradiation.

Due to a general lack of chemical indicators for UV sterilization, chemicals that exhibited an easily visualized color and/or fluorescence change upon UV irradiation were sought. These chemical dyes needed to be water soluble, as most UV sterilization is performed either on dry surfaces or in an aqueous media; exhibit a high extinction coefficient, such that the dyes are easily visualized with the naked eye; and preferably be non-toxic. The highly colored FD&C dyes appeared to meet all of the requirements with very low levels of toxicity and high water solubility.

To characterize how these dyes would degrade upon UV irradiation, the representative fluorescein (D&C Yellow 8) was first chosen. Various concentrations of fluorescein were irradiated in quartz cuvettes by 254 nm UV germicidal bulbs. The fluorescence intensity, absorbance and UV dose was measured throughout the experiment. The curves were fitted using TableCurve2D and found to fit best to a decay type of curve. As shown in FIG. 1a, each concentration of fluorescein exhibited a good fit with this decay curve.

Figure 1B:
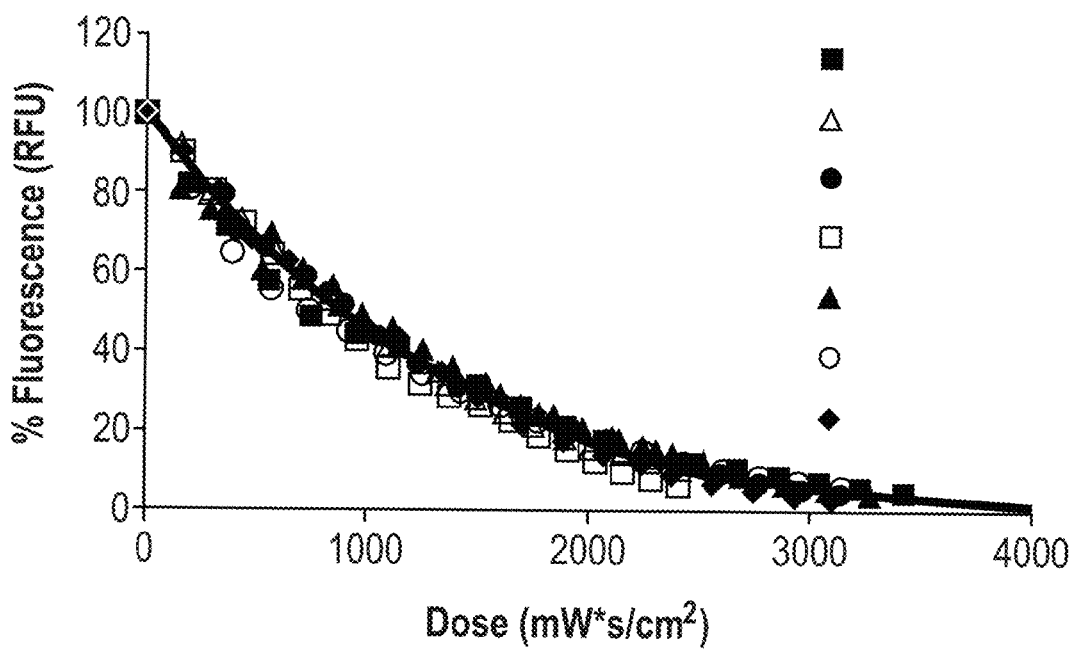

As with any decay, when the fluorescence intensity of each curve was converted into a percentage of its starting value, all of the curves collapsed onto the save curve (FIG. 1b). The collapsed absorbance and fluorescent intensity curves were similar. Utilizing a single fitted line equation greatly simplifies the execution and analysis of experiments, as the exact concentration of the dye does not need to be known, only an initial measurement of its absorbance or intensity. However, the starting and ending values must be within the linear range of the detector.

To identify other dyes that exhibit a similar simple decay curve when exposed to 254 nm UV light and had different sensitivities such that they would be able to quantitate a range of different doses, Erythrosin B (FD&C Red 3), Allura Red (FD&C Red 40), Brilliant Blue FCF (FD&C Blue 1), Indigo Carmine (FD&C Blue 2), Tartrazine (FD&C Yellow 5), Sunset Yellow FCF (FD&C Yellow 6) and Fast Green FCF (FD&C Green 3) were chosen. First, the absorbance spectrum, the peak absorbance wavelength and the linear region of detection of each chromophore was determined (see Supporting Information).

For the UV degradation studies, a concentration of 10 µg/mL was chosen to ensure that each dye was well within the linear range of detection. Similar to the studies with fluorescein, each dye was subjected to known amounts of UV light and the absorbance was measured throughout the experiment. Erythrosin B also had a significant fluorescence emission that could be used in addition to its absorbance. The absorbance values were converted into a percentage of the original absorbance value and the resulting curves were fitted with the same Decay curve as fluorescein.

Figure 2:
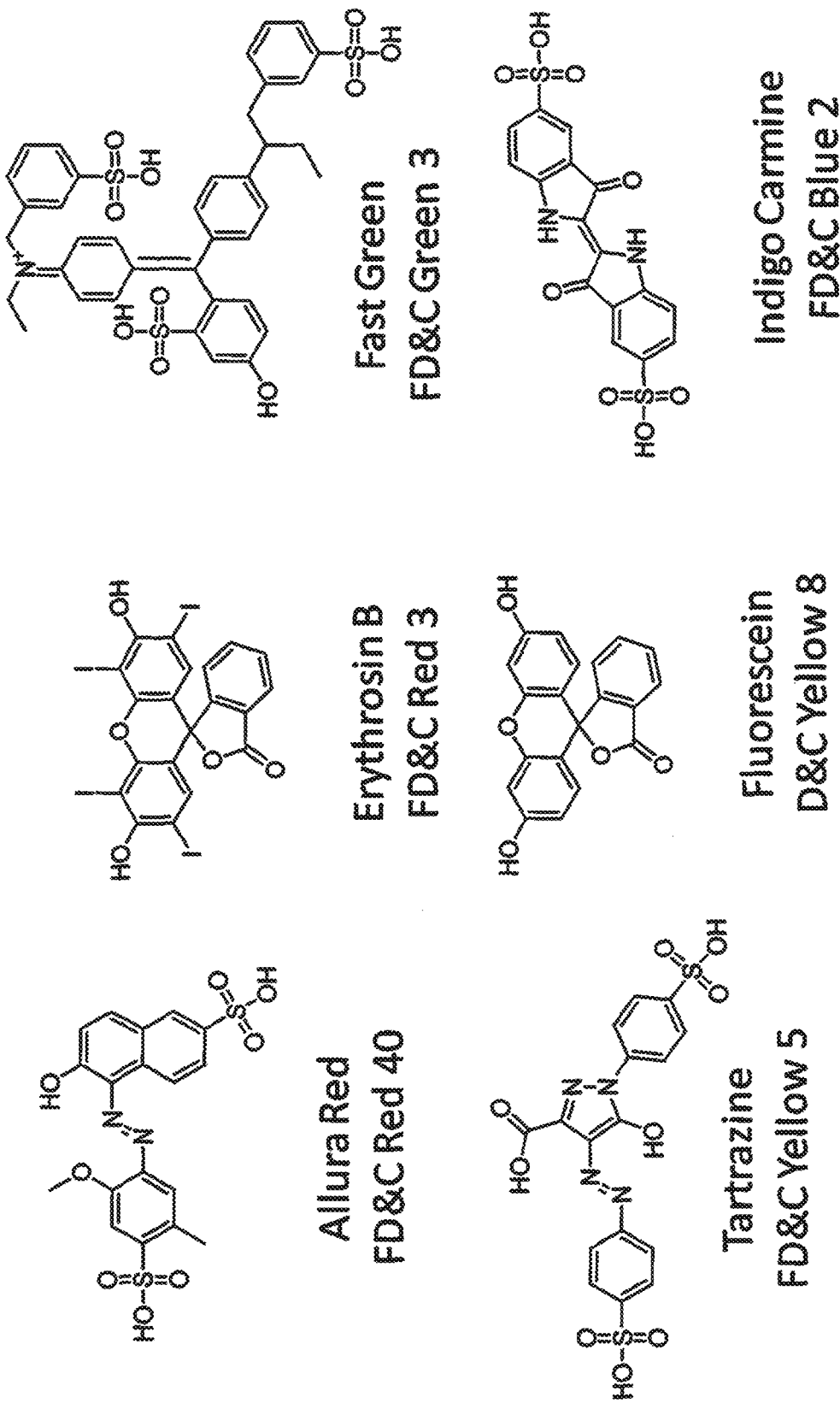
FIG. 2 exemplary chemical Structures of chromophores and fluorophores.
Figures 3A, 3B:
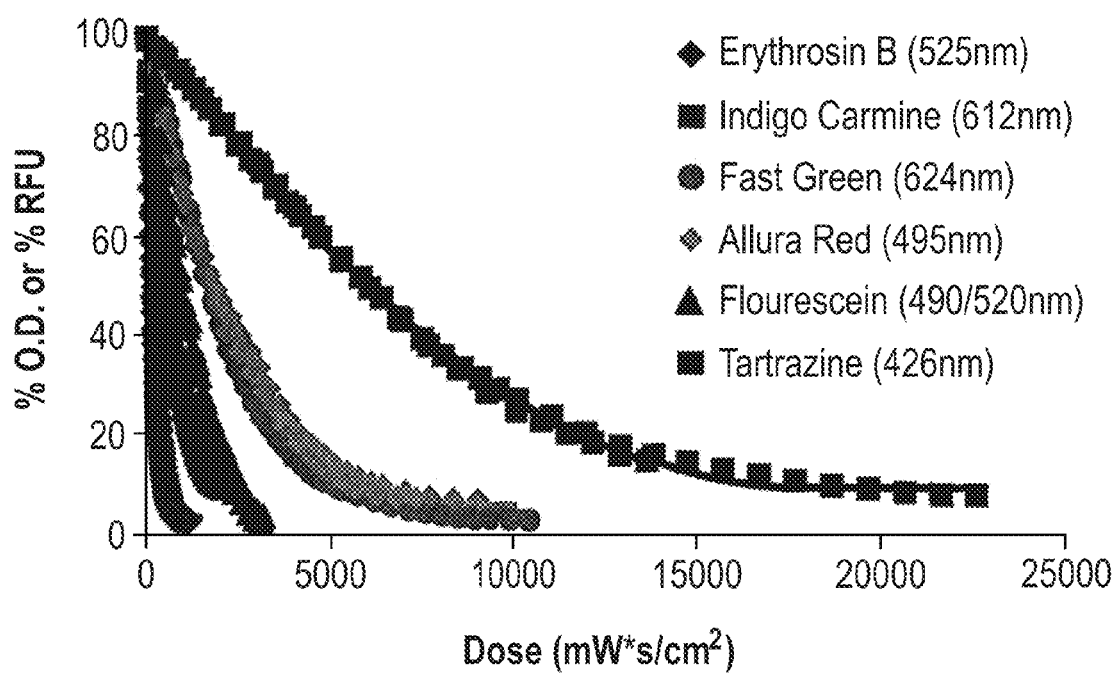
FIG. 3 are exemplary curve representing independent experiments depicting A.) The loss of absorbance or fluorescence intensity from 10 mg/mL chomophores and 3.5 mg/mL fluorescein upon irradiation with known doses of 254 nm UV light as a percentage of the starting value. The absorbance or excitation and emission wavelengths are shown for each dye in parenthesis. Each curve represents three independent experiments. B.) UV dose quantitation range for each dye.

Sunset Yellow and Erioglaucine were found to not exhibit a simple decay curve and therefore were not used in any further experiments. The remaining dyes that did exhibit a simple decay curve can be seen in FIG. 2. As shown in FIG. 3a, the decay rate of the various dyes that did exhibit simple decay curves spanned a broad range of UV doses. The quantitation range of each dye was determined to be between the doses that yielded a percentage value between 100% and ~20% of the original absorbance value (FIG. 3b). With standard curves generated and quantitation ranges identified, these dyes then could be used to quantitate the amount of UV dose actually realized within an irradiated object.

UV sterilization is most efficacious when applied to a low UV absorbance medium such as air. However, most sterilization applications, especially liquid sterilization processes require the UV light to pass through some kind of container in addition to the medium itself. Inconsistencies in the absorbance of the package due to changes in the thickness or the type of material can lead to areas with a much lower UV dose. Similarly, heterogeneous solutions also can cause differing levels of UV dose within itself.

While the UV dose irradiating the exterior of a container is fairly straightforward to measure via bulb power, the ability to measure the average cumulative dose within a container is not so easily accomplished. However, with a soluble dye that can be placed within a container, the approximate average dose obtained within that container upon UV irradiation can be determined.

To study the impact of uneven material absorbance upon sterilization, quartz cuvettes were unevenly wrapped with various plastic sheets. This wrapping contained creases, small folds and gaps which provided differences in the absorbance of UV light. Ten different wrappings were applied and organized into groups with decreasing average UV transmission (FIG. 4a).

To the wrapped cuvettes, 1.5 mL of a ~1×$10^6$ CFU/mL solution of organisms or 10 µg/mL solution of the dye Erythrosin B were added. Both organisms and dye were suspended in Dulbeco's modified phosphate buffered saline containing 0.05% Tween-80 (TDPBS). TDPBS was used to keep the organisms from forming large clumps and also to impart a significant UV absorbance to the solution itself. The filled, wrapped cuvettes then were irradiated with a constant external dose as measured by the bulb power and the surviving number of organisms or the internal dose as measured by the reduction in dye absorbance was determined.

The gram negative bacteria, *E. Coli*, the gram positive bacteria, *Staphylococcus aureus* and the yeast *Candida albicans* were chosen for this sterilization experiment. UV doses that provide for a 12-log overkill sterilization were obtained or calculated from published data. Due to differences in methodology and the inherent challenges of measuring UV doses, a large variation in the overkill sterilization dose was present in the literature with doses for *E. coli* ranging between 2.5 to 98 mW*s/cm$^2$ (25,26,27,28,31), *S. aureus* between 2.7 to 174 mW*s/cm$^2$ (25,26,27,29,30,31) and *C. albicans* between 26 to 537 mW*s/cm$^2$ (25,26,31). With regards to the various published values and our own unpublished data, a dose of 100 mW*s/cm$^2$ was chosen for the bacteria and a dose of 250 mW*s/cm$^2$ was chosen for *C. albicans*.

Figure 4A:
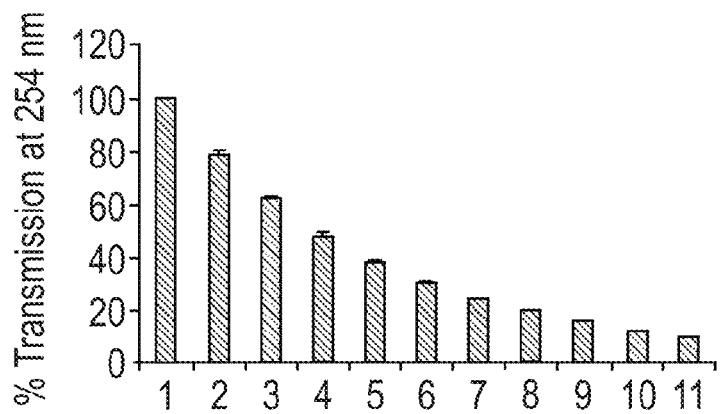
FIG. 4 are exemplary container groups with various plastics unevenly wrapped to partially block UV light. A.) The UV % transmission of the material(s) of each group of containers. B, C, D.) The inhibition of UV transmission and the corresponding loss of sterilization of *Escherichia coli* (B.), *Staphylococcus aureus* (C.) and *Candida albicans* (D.). The total irradiance of each group (n=6) was 100 mW*s/cm$^2$ for the bacteria (B,C.) and 250 mW*s/cm$^2$ for *C. albicans* (D.) as measured by the power output of the UV bulbs. The UV dose within the container was calculated by the degradation of Erythrosin B (white bars) and the number of viable organisms remaining after irradiation was determined (black bars). All error bars represent standard error.
Figure 4B:
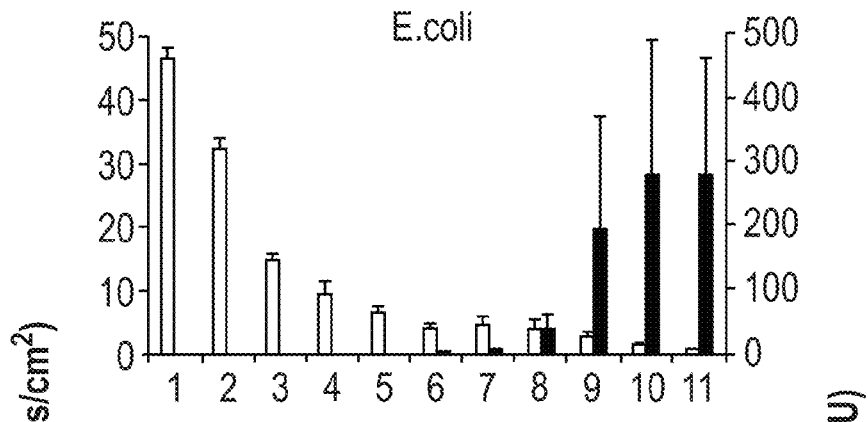
Figure 4C:
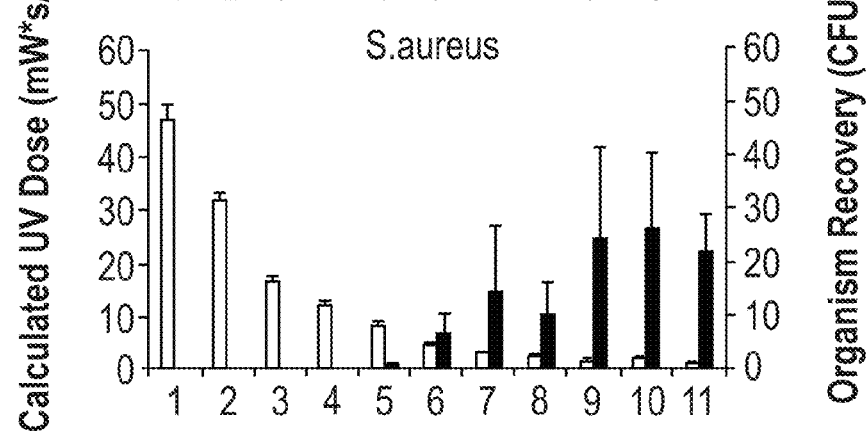
Figure 4D:
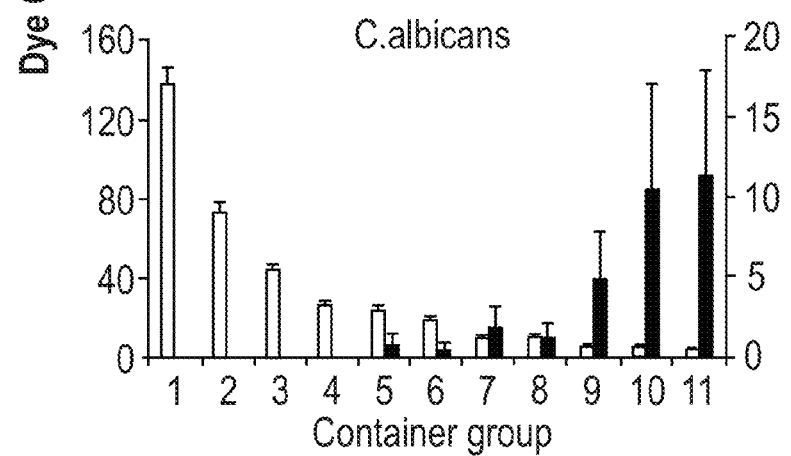

As can be seen in FIG. 4*b-d*, the calculated internal dose was less than the applied dose and as the transmission of the plastic wrapping decreased (higher container group numbers have lower UV transmission as shown in FIG. 4*a*), the internal dose showed a similar decrease. The lower internal dose, even in an unwrapped cuvette (container group 1) is most likely due to the increased absorbance of the TDPBS solution itself, almost a 20% decrease in transmission per cm. An increase in distance from the bulb to account for the wrappings on other cuvette groups and the slight absorbance of the cuvette itself all contribute to the lower internal dose.

The container groups that exhibited high transmission and corresponding higher internal doses showed complete sterilization for all three organisms (container groups 1-4). However, as the absorbance of the plastic wrapping increased, the internal dose eventually dropped to a level at which some of the organisms could survive (container groups 5-7). Once this transition point was reached, the number of surviving organisms increased as the internal dose dropped further (container groups 8-11). The surviving organisms were not evenly distributed between the replicates of each sample due to the uneven wrapping of the plastic, leading to the high variability.

In addition to being used as a quantitative measurement tool, the degradation of the dyes also can be used in a more qualitative manner as a visual chemical indicator of UV dose. Since highly colored FD&C dyes were chosen, the color transition while the dye is degrading can be used as a visual indicator. To show the visual changes, several concentrations of various dyes were irradiated with known doses of UV light with images of each dye taken throughout the irradiation process. A 10 and 100 µg/mL solution of Erythrosin B and a 100 µg/mL solution of Indigo Carmine were chosen as representative candidates as they showed good visual color changes in the range of doses tested.

Figure 5B:
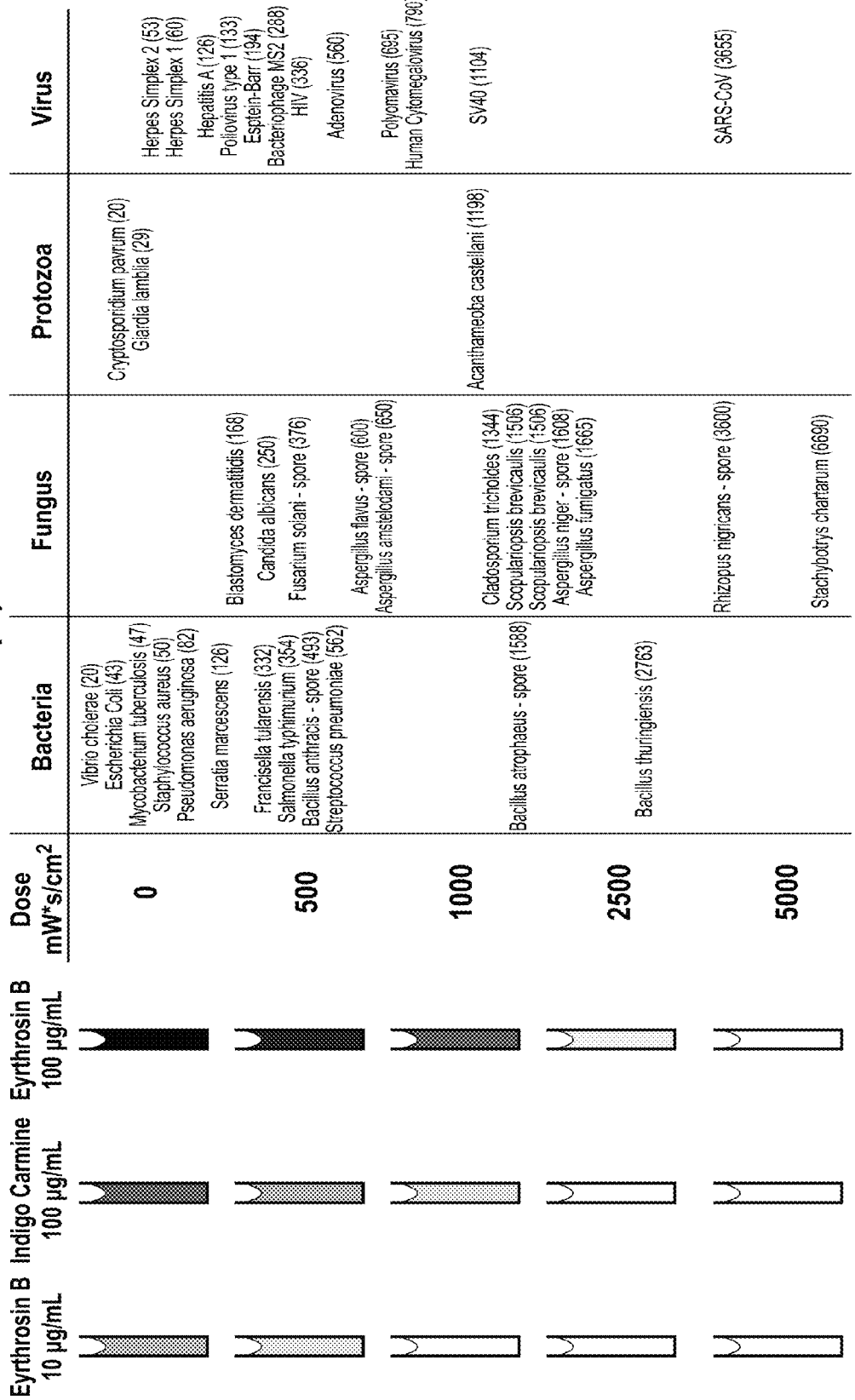
FIG. 5(B) is a schematic representation of FIG. 5(A).
Figure 6A:
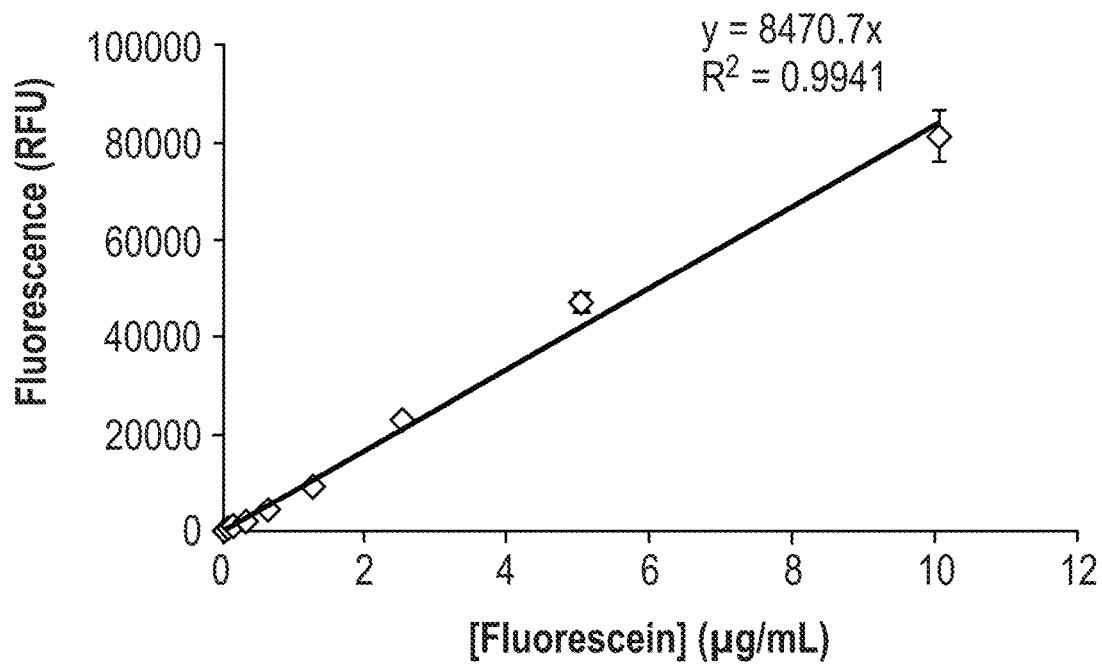
FIG. 6A-6K are charts depicting the effects of exemplary doses of UV radiation and their respective effects as tested.
Figure 6B:
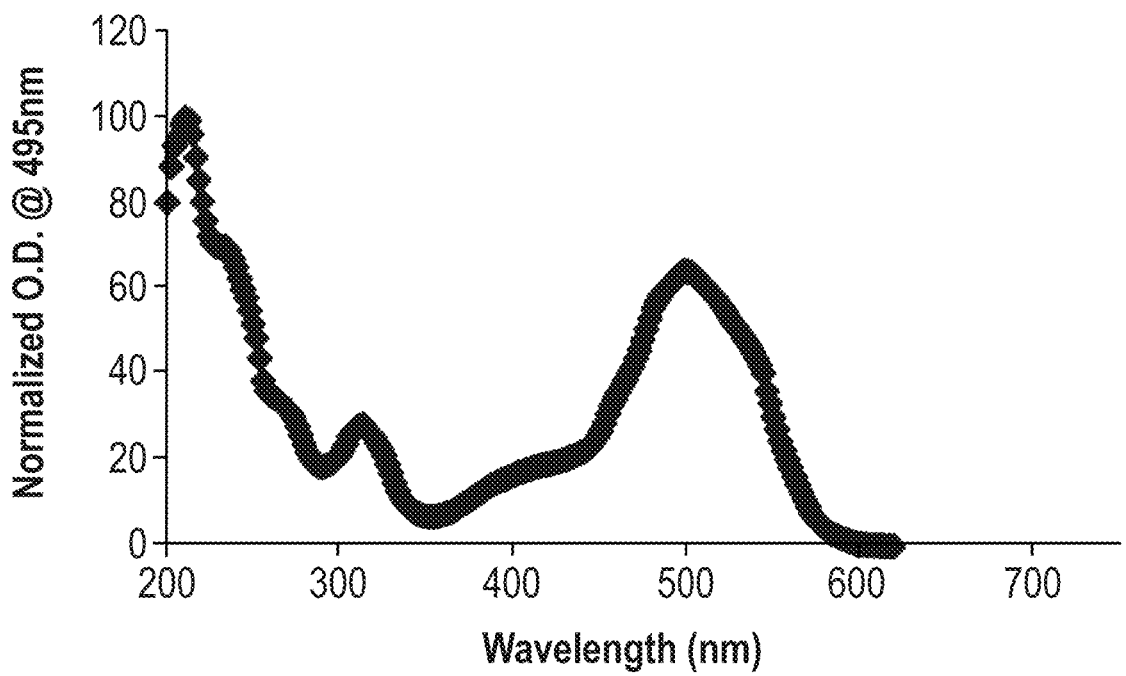
Figure 6C:
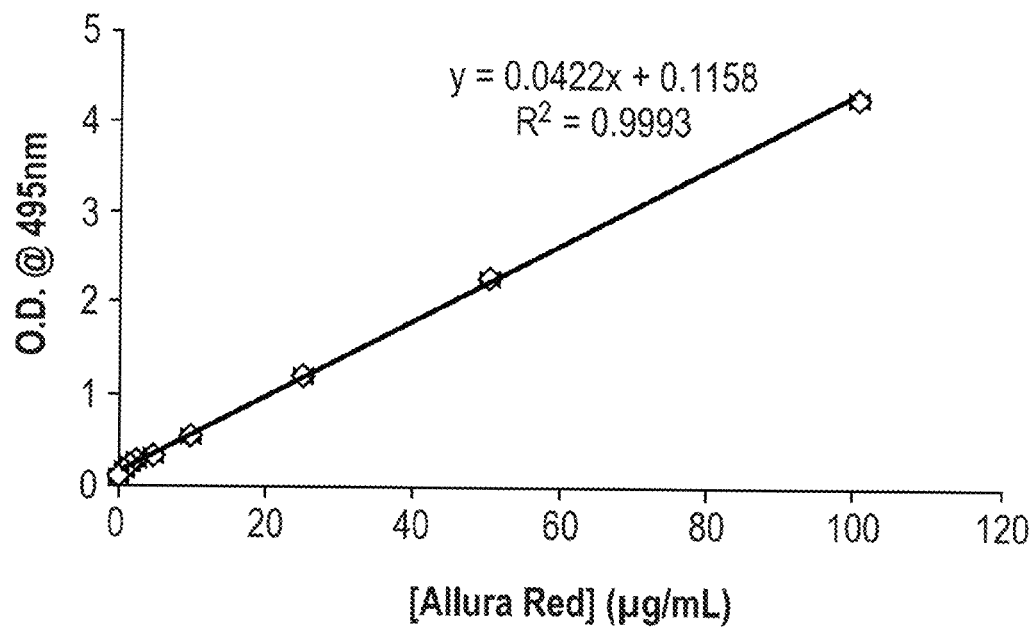
Figure 6D:
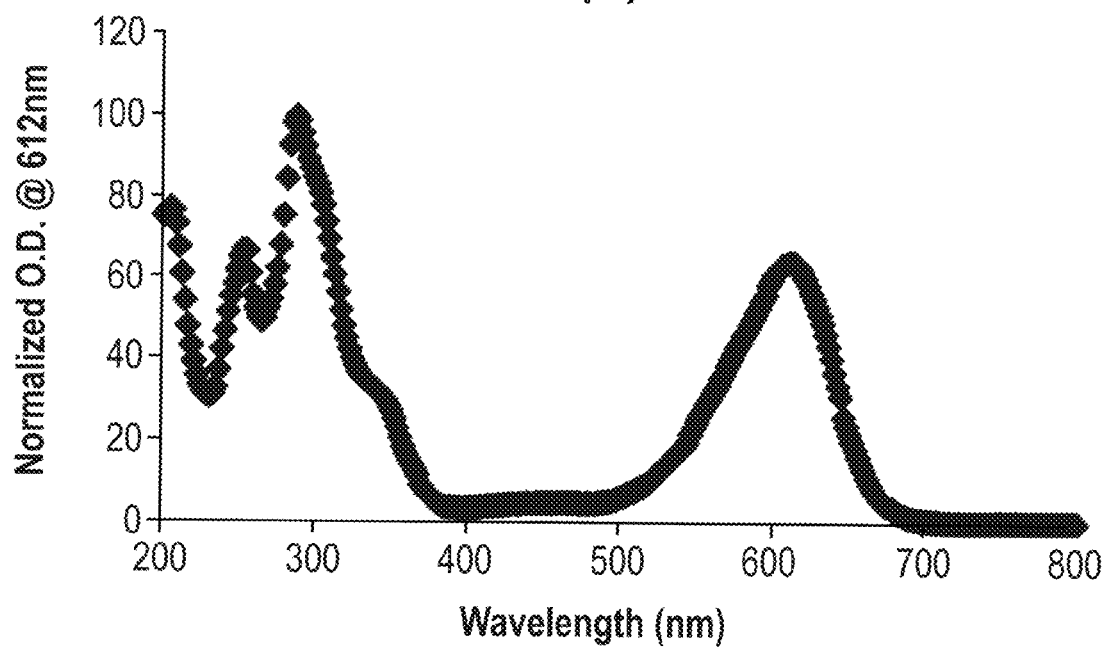
Figure 6E:
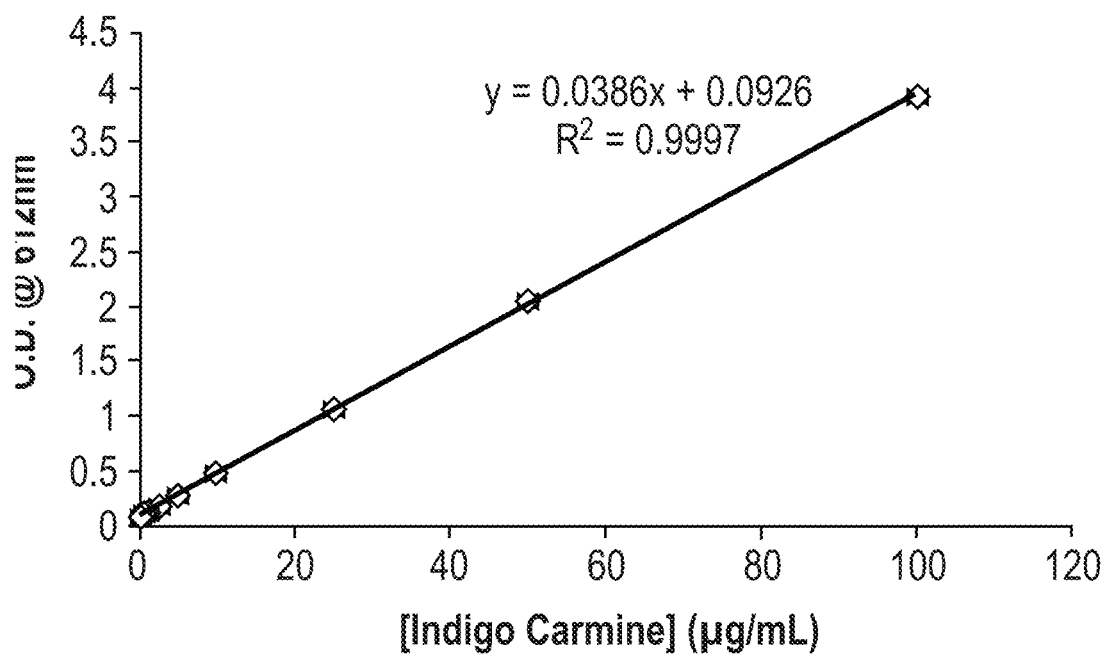
Figure 6F:
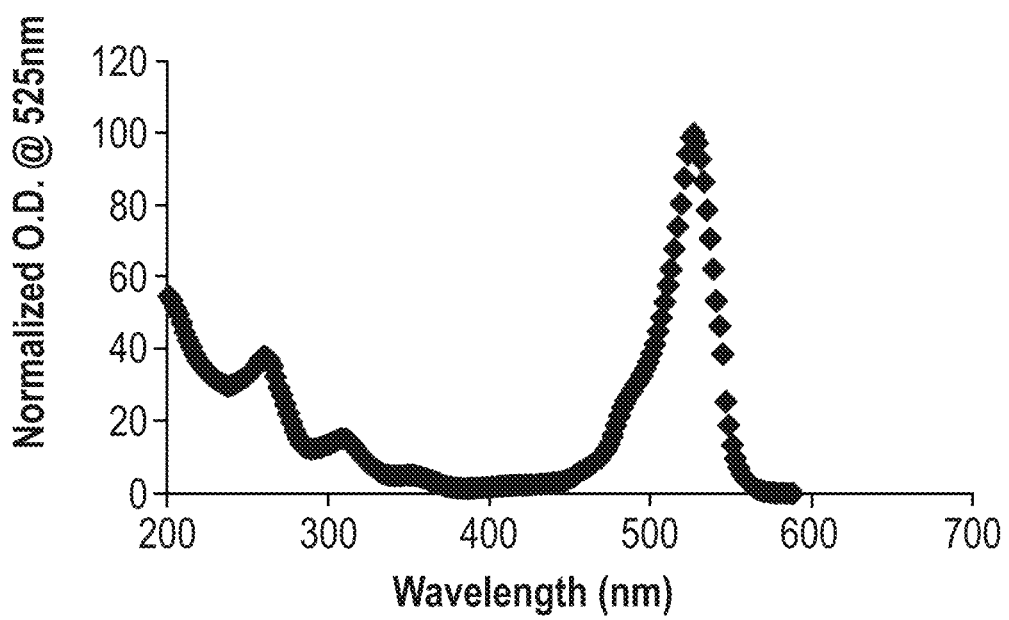
Figure 6G:
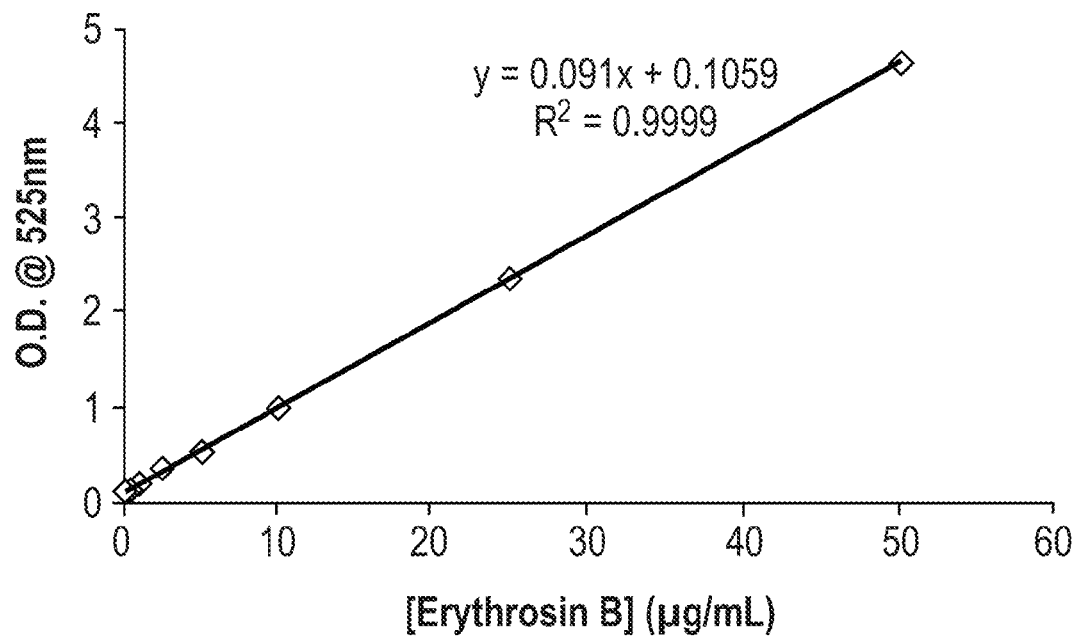
Figure 6H:
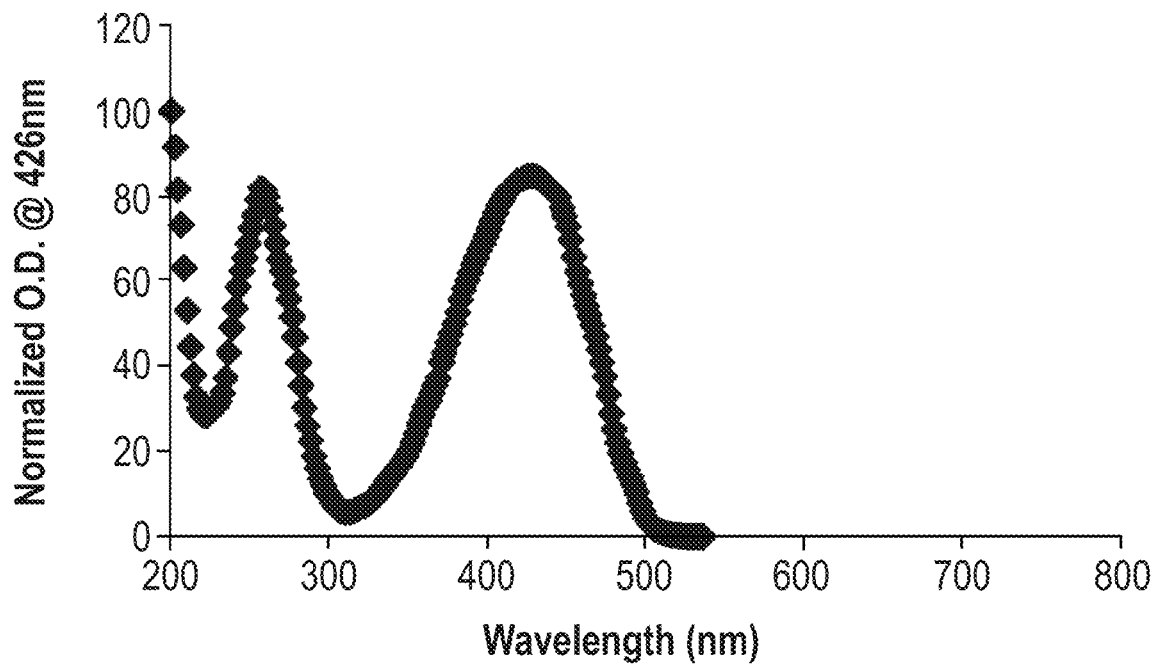
Figure 6I:
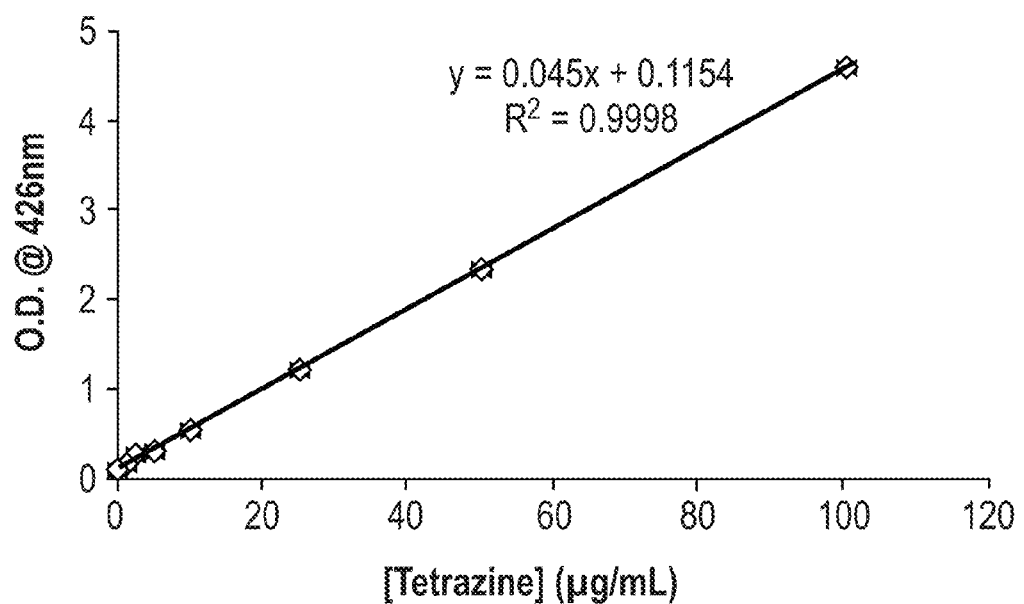
Figure 6J:
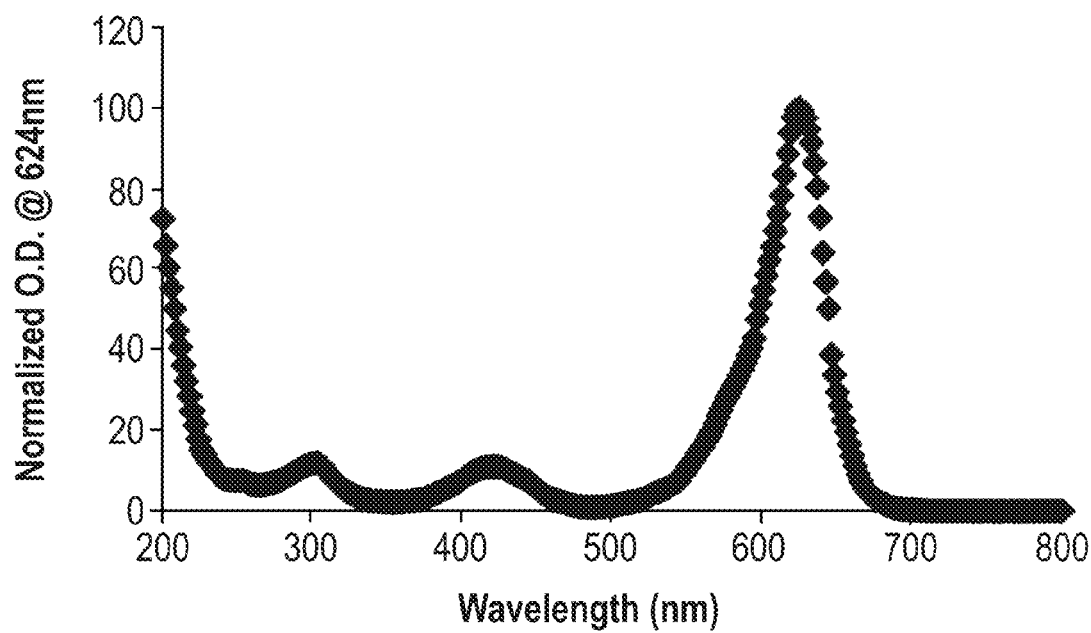
Figure 6K:
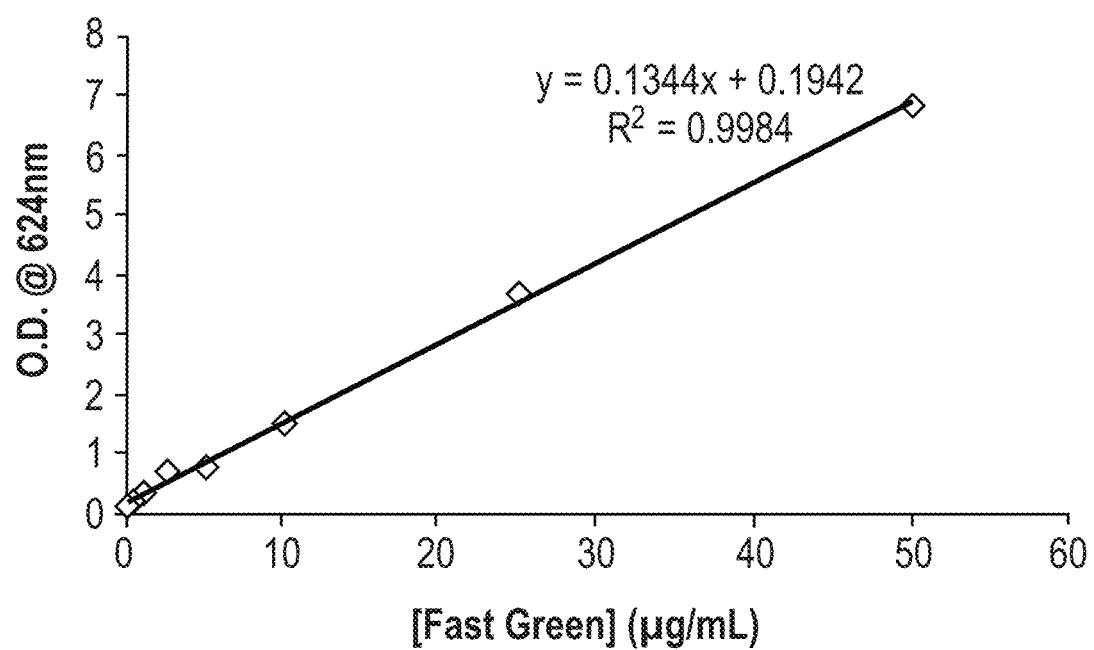

As shown in FIGS. 5(A) and (B), a 10 µg/mL solution of Erythrosin B exhibited the most visual change at lower UV doses with a stark difference in color between 0 and 500 mW*s/cm$^2$ and complete loss of color by 1000 mW*s/cm$^2$. A 100µg/mL solution of Indigo Carmine was slightly less sensitive showing a slight color change at 500 mW*s/cm$^2$, a stark color change by 1000 mW*s/cm$^2$ and a complete loss of color by 2500 mW*s/cm$^2$. Lastly, a more concentrated 100 µg/mL solution of Erythrosin B allowed for visual changes with higher doses of UV light as a complete loss of color was not observed until a 5000 mW*s/cm$^2$ dose. The less UV sensitive dyes could be used as visual indicators if higher UV doses are required.

As a reference, the 12-log overkill sterilization dose values for various bacteria, fungi, viruses and protozoa were obtained or calculated from published data (31). These organisms were chosen for either their use as a biological indicator for UV sterilization or because they are known human pathogens. In general, most bacteria, viruses and protozoa are sterilized with less than 500 mW*s/cm$^2$ of UV with a few organisms harboring increased resistance. Fungi, especially in their spore form are more resistant to UV sterilization than the other groups of organisms with the majority of organisms sterilized between 500 and 2500 mW*s/cm$^2$. As the vast majority of organisms are sterilized within the 0 to 5000 mW*s/cm$^2$ range, Erythrosin B and/or Indigo Carmine can be used as an effective visual qualitative chemical indicator to determine whether the UV dose was sufficient for sterilization.

Seven FD&C dyes and the D&C dye fluorescein were tested to determine if their absorbance and/or fluorescence degradation upon irradiation with 254 nm UV light could be used as a quantitative measurement of UV dose. Six of the eight dyes showed simple decay curves upon UV irradiation. Standard UV degradation curves of these six dyes were created and all of these dyes could be used to determine the average UV dose imparted to a solution. Due to the different sensitivities of the dyes, different ranges of UV dose could be quantified.

To exhibit the potential of directly measuring the UV dose within a container, cuvettes unevenly wrapped with various UV absorbing plastics were irradiated with a constant dose of UV energy that was equivalent to a 12-log overkill sterilization dose. Due to the construction of the cuvette containers, the amount of UV energy that is able to enter into the internal space is unknown and difficult to absolutely calculate. To these containers, the dye Erythrosin B or the microorganism *E. coli, S. aureus* or *C. albicans* was added. The dye was used to quantitate the internal UV dose or the number of surviving organisms was determined. The loss of internal dose was shown to correlate to the increase in the number of surviving organisms even though the total UV energy delivered to the containers' exterior did not change.

Finally, the visual changes of the dyes upon UV irradiation were studied. The two most sensitive dyes, Eyrthrosin B and Indigo Carmine showed good visual color changes in the dose range of 0 to 5000 mW*s/cm$^2$ depending on their concentration. Additional dyes could be used if larger doses were required, however since most relevant microorganisms' 12-log overkill sterilization dose is below 5000 mW*s/cm$^2$ these two dyes should be applicable to the vast majority of microorganisms.

In summary, the challenges in measuring the absolute UV dose and the current dearth of commercially available chemical indicators for UV sterilization present a need for new quantitative and qualitative methods. The ability to utilize FD&C dye degradation as both a quantitative measurement tool and a qualitative visual indicator makes these dyes a good choice for a UV chemical indicator.

A number of embodiments of the present invention have been described. While this specification contains many specific implementation details, there should not be construed as limitations on the scope of any inventions or of what may be claimed, but rather as descriptions of features specific to particular embodiments of the present invention.

Certain features that are described in this specification in the context of separate embodiments can also be implemented in combination in a single embodiment. Conversely, various features that are described in the context of a single embodiment can also be implemented in combination in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order show, or sequential order, to achieve desirable results. In certain implementations, multitasking and parallel processing may be advantageous. Nevertheless, it will be understood that various modifications may be made without departing from the spirit and scope of the claimed invention.

The invention claimed is:

1. A method of quantifying UV disinfecting doses adequate for sterilizing an ophthalmic lens using one or more additive indicators, the method comprising the steps of:
   adding one or more water soluble and non-toxic indicators to an aqueous solution containing an ophthalmic lens;
   applying a dose of ultraviolet radiation for a controlled time and intensity to the aqueous solution containing the ophthalmic lens; and
   gathering feedback from the degradation of at least one of chromophores and fluorophores of the one or more of the water soluble and non-toxic indicators to determine the actual dose of ultraviolet radiation imparted to the aqueous solution and ophthalmic lens combination, the feedback being at least one of quantitative or qualitative nature.

* * * * *